United States Patent [19]  [11] 4,122,184
Soper  [45] Oct. 24, 1978

[54] BENZIMIDAZOLE INSECTICIDES

[75] Inventor: Quentin F. Soper, Indianapolis, Ind.

[73] Assignee: Eli Lilly and Company, Indianapolis, Ind.

[21] Appl. No.: 862,890

[22] Filed: Dec. 21, 1977

Related U.S. Application Data

[60] Continuation of Ser. No. 397,496, Sep. 14, 1973, abandoned, which is a division of Ser. No. 190,294, Nov. 18, 1971, abandoned, which is a continuation-in-part of Ser. No. 812,449, Apr. 1, 1969, abandoned, which is a continuation-in-part of Ser. No. 726,540, May 3, 1968, abandoned.

[51] Int. Cl.$^2$ ............................................. A01N 9/22
[52] U.S. Cl. .................................. 424/273 R; 548/332
[58] Field of Search .......................................... 424/273

[56] References Cited

U.S. PATENT DOCUMENTS 3,542,923  11/1970  Newbold et al. ................. 260/309.2

FOREIGN PATENT DOCUMENTS 659,384  5/1965  Belgium.

*Primary Examiner*—V. D. Turner
*Attorney, Agent, or Firm*—James L. Rowe; Everet F. Smith

[57] ABSTRACT

2,6-Di(fluoroalkyl)-4-nitrobenzimidazoles and certain N-acyl derivatives thereof, including sulfonates, thiocarboxamides, and carboxylates, are used to control a broad spectrum of mites and insects with particularly good effect against members of the orders Hemiptera, Coleoptera, Orthoptera, and Lepidoptera.

8 Claims, No Drawings

BENZIMIDAZOLE INSECTICIDES

CROSS-REFERENCE

This application is a continuation of my then copending application Ser. No. 397,496, filed Sept. 14, 1973, now abandoned, which was a division of my then copending application Ser. No. 190,294, filed Nov. 18, 1971, now abandoned, which was a continuation-in-part application of my then copending application Ser. No. 812,449 filed Apr. 1, 1969, now abandoned, which was in turn a continuation-in-part application of my then copending application Ser. No. 726,540, filed May 3, 1968, now abandoned.

BACKGROUND OF THE INVENTION

Benzimidazoles are known to be useful in combating intestinal parasites of mammals and birds. Furthermore, 2-trifluoromethylbenzimidazoles have been found to be useful as herbicides, nematocides, molluskicides, and insecticides. [British Pat. No. 1,087,561; U.S. Pat. No. 3,412,101; South African Pat. No. 65/5584; Netherlands Pat. No. 67,13786; (Derwent Basic No. H2118) are exemplary.] The 2-trifluoromethyl derivatives most frequently employed as insecticides have been substituted in the benzene portion of the benzimidazole ring system with chlorine and nitro groups, with the most active compounds being 2-trifluoromethyl-4,5,6,7-tetrachlorobenzimidazole, 2-trifluoromethyl-5,6-dichlorobenzimidazole, and phenol 2-trifluoromethyl-4-nitro-6-chloro-1-benzimidazolecarboxylate. In general these compounds have shown their greatest activity against insects of the order Lepidoptera, such as Southern armyworm, and of the order Diptera, such as house flies and mosquitoes. For example, 2-trifluoromethyl-4,5-dichlorobenzimidazole gives a complete kill of Southern armyworm larvae at 250 ppm, but is without action against milkweed bugs, oriental roaches and boll weevils at that same concentration, and in fact, its activity against house flies is excellent only at 1000 ppm. The isomeric compound, 2-trifluoromethyl-5,6-dichlorobenzimidazole, has the same excellent activity against Southern armyworm larvae at 250 ppm, but no activity at the same level against milkweed bugs, house flies, oriental roach and boll weevil. In general, these chlorinated benzimidazoles do not approach, in absolute activity, the organic phosphate insecticides, nor do they have the same broad spectrum of action.

Two large classes of marketed insecticides which have been widely used and which have a reasonably broad spectrum against many orders of insects plus a low dosage range are the organic phosphates and the chlorinated hydrocarbons. Many of the most active of the organic phosphate insecticides are extremely toxic to humans and their toxicity by intradermal absorption is of the same order of magnitude as their toxicity by inhalation. Thus, these very toxic compounds are extremely dangerous to handle, even when using a gas mask or oxygen mask. The safest of the phosphorous insecticides, malathion, is still widely used, but its spectrum is not as broad as would be desirable and many species of insects or mites have become resistant to it over the years.

The deficiencies of the chlorinated hydrocarbons are of a different nature. Resistance is, of course, prevalent, but this problem is not as serious as might be expected because of the endless succession of new chlorinated hydrocarbons which have beend produced. The chief drawback to the use of chlorinated hydrocarbons is their persistance in soil and water for many, many years, attributed chiefly to their metabolic stability. This persistance has now begun to affect other forms of life, including birds and fish.

Thus, there is a need for compounds with both insecticide and miticide activity, which have a broad spectrum, are safe to handle and are non-persistant.

SUMMARY OF THE INVENTION

This invention provides a method for killing mites and insects of the orders Coleoptera, Lepidoptera, Hemiptera and Orthoptera, and flies and mosquitoes, comprising the application to the insect or mite habitat of a composition containing, as its biocidally effective ingredient, a benzimidazole represented by the following formula:

wherein R is hydrogen,

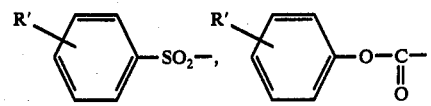

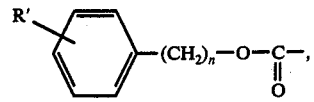

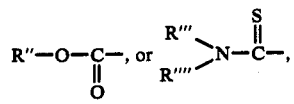

wherein R' is hydrogen, fluorine, chlorine, bromine, $C_1-C_5$ alkoxy, $C_1-C_5$ alkyl or nitro; R" is $C_1-C_8$ alkyl, halo-substituted $C_1-C_5$ alkyl, halo-substituted $C_2-C_5$ alkenyl, $C_2-C_5$ alkynyl or $C_2-C_5$ alkenyl; R'" and R"" individually are hydrogen, $C_1-C_5$ alkyl or phenyl, and when taken together a pentamethylene or tetramethylene chain; Y is F or H; Z is F, H, Cl, —$CF_3$ or —$CF_2$—$CF_3$; and halo is a halogen having an atomic number below 36.

In the above formula, it will be recognized that when R is hydrogen, the benzimidazole exists in two tautomeric forms, one of which is named (when Y and Z are F) 2,6-bis(trifluoromethyl)-4-nitrobenzimidazole and the other 2,5-bis(trifluoromethyl)-7-nitrobenzimidazole. Both of these structures exist in equilibrium in any preparation of the pure compound. When the hydrogen on the benzimidazole nitrogen is replaced by phenylsulfonyl, carboxylate, thiocarboxamide or other radical comprehended within the term "R" as defined above, there is no longer the possibility for tautomerism and each preparation of the N-derivative contains a mixture of two substances, one of which would be named, for example, using the same compound as above for illustrative purposes only, 2,6-bis(trifluoromethyl)-4-nitro-1-phenylsulfonylbenzimidazole and the other would be 2,5-bis(trifluoromethyl)-7-nitro-1-phenylsulfonylbenzimidazole. Only one of the two isomers may be readily isolatable. It should be understood that this invention includes within its scope both the 1-substituted-4-nitro-6-fluoromethyl-2-fluoroalkylbenzimidazoles and the 1-substituted-7-nitro-5-fluoromethyl-2-fluoroalkylbenzimidazoles.

In the above formulas, "halo" can be chlorine, bromine, or fluorine. When R' is $C_1$-$C_5$ alkoxy, it can be methoxy, ethoxy, isopropoxy, n-propoxy, sec-butoxy, n-butoxy, isobutoxy, n-amyloxy, isoamyloxy or sec-amyloxy; and when R', R''' or R'''' are $C_1$-$C_5$ alkyl, they can be methyl, ethyl, n-propyl, isopropyl, n-butyl, isobutyl, sec-butyl, t-amyl, n-amyl or sec-amyl. When R''' and R'''' together form a pentamethylene or tetramethylene chain, the resulting group is piperidino or pyrrolidino. Groups illustrating the scope of R'' include those specified for $C_1$-$C_5$ alkyl above, plus n-hexyl, isohexyl, t-octyl, n-heptyl, and the like, as well as $C_2$-$C_5$ alkenyl groups including vinyl, 1-propenyl, isopropenyl, allyl, crotyl, methallyl, 2-pentenyl, and the like, and $C_2$-$C_5$ alkynyl groups including ethynyl, 1-propynyl, 1-butynyl, 1-methyl-1-butynyl and the like. When R'' is halo-substituted $C_2$-$C_5$ alkenyl or halo-substituted $C_1$-$C_5$ alkyl, it can be any of the above groups used to illustrate the scope of the terms $C_2$-$C_5$ alkenyl or $C_1$-$C_5$ alkyl substituted with one or more halogens including chlorine, bromine and fluorine. Typical groups illustrating the above terms include chloroallyl, trifluoromethyl, chloromethyl, dichloromethyl, α-bromoethyl, α-chlorohexyl, perfluoro-n-octyl, 1,2-dichloro-2-methylbutyl, 2,3-dichloro-4,4-dimethylpentyl, 3-bromo-1-pentenyl and the like. When Y or Z are H or F, the resulting substituents are difluoromethyl and trifluoromethyl respectively. When Z is Cl, $CF_3$, or $C_2F_5$, the resulting substituent at 2 is chlorodifluoromethyl, pentafluoroethyl or heptafluoropropyl.

In a second aspect of this invention, compounds according to the above formula in which R is other than hydrogen are novel and are found to be useful as insecticides as will be indicated hereinafter. These compounds will have the formula:

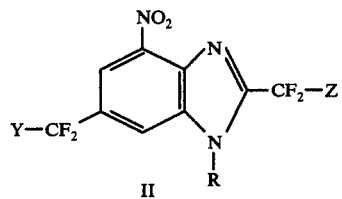

wherein Q is

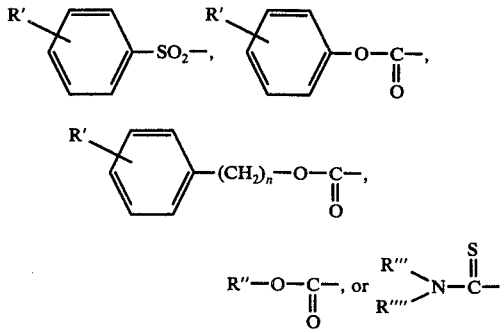

wherein R' is fluorine, chlorine, bromine, $C_1$-$C_5$ alkoxy, $C_1$-$C_5$ alkyl or nitro; R'' is $C_1$-$C_5$ alkyl, halo-substituted $C_1$-$C_5$ alkyl, halo-substituted $C_2$-$C_5$ alkenyl, $C_2$-$C_5$ alkynyl or $C_2$-$C_5$ alkenyl; R''' and R'''' individually are hydrogen, $C_1$-$C_5$ alkyl or phenyl, and when taken together a pentamethylene or tetramethylene chain; Y is F or H; Z is F, H, Cl, $-CF_3$ or $-CF_2-CF_3$; and halo is a halogen having an atomic number below 36.

The 4-nitro-6-fluoromethyl isomer is indicated by the above formula. This invention also claims within its scope the 7-nitro-5-fluoromethyl isomer prepared by reaction of the acylating agent with the nitrogen in the ring adjacent to the nitro group. These compounds are represented by Formula III wherein Z, Q, R', R'', R''', and R'''' all have the same meaning as before.

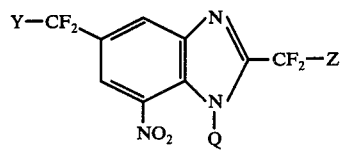

Compounds represented by the Formulas II or III are conveniently prepared by reacting the sodium salt of the parent benzimidazole with the appropriate benzenesulfonyl chloride or aryl or aliphatic chloroformate, or thiocarbamoyl chloride.

In carrying out the processes of this invention, an insecticidal or miticidal amount of a benzimidazole according to Formula I above is applied to the insect or mite habitat, which habitat might be, for example, the foliage or other parts of a living plant when aphids, mites, milkweed bug or the like are to be combated, or the soil in which a crop has been planted, as when it is desired to combat corn rootworm or the like. Again, the insect habitat might be the wall of a building when it is desired to combat flies or mosquitoes.

A benzimidazole according to the above formula can be applied to the mite or insect habitat in pure or relatively pure form if desired; that is to say, unmixed with other constituents. Such method of application is, however, wasteful inasmuch as the compounds are active at such extremely low rates, as will be delineated hereinafter. Thus, the insecticidal and miticidal properties of 2-fluoroalkyl-6-fluoromethyl-4-nitrobenzimidazoles and their N-derivatives are preferably secured by application of a formulation containing the benzimidazole as the active agent dispersed in a suitable inert carrier, with or without compatible fungicidal, bactericidal, insecticidal, acaricidal or herbicidal ingredients.

Benzimidazole-containing compositions are most satisfactorily formulated as emulsifiable concentrates or dusts, although a granular formulation or wettable powder can also be used. Those compositions which are adapted for direct spraying or dusting upon the insect or mite habitat are prepared by methods well known to the art, as for example by mixing the benzimidazole with a non-phytotoxic diluent such as water plus a surface-active agent to provide an emulsifiable concentrate, or such as clay, bentonite, silica, hydrous alumina, kieselguhr, or diatomaceous earth to provide a dusting powder or wettable powder where a surfactant is included or with one of these latter ingredients followed by compression of the resulting mixture to provide a granular formulation. The dusting powder and granular formulations are customarily used as such, but wettable powders and emulsifiable concentrates are first prepared as a concentrate and then further diluted with a non-phytotoxic material prior to use. The insecticidally active benzimidazole is customarily present in the diluted dust or spray in a concentration varying from about 0.0025 percent to upwards of about 5 percent or preferably from 0.01–0.6 percent. The concentration of benzimidazole in concentrates used for preparing wettable powders or emulsifiable concentrates is necessarily far higher and can vary from 5 percent up to as high as 80 or 90 percent if desired. The above insecticidally-active compositions are applied to the insect or mite habitat by means of spray guns, dust guns, spreaders or the like.

The amount of benzimidazole to be applied for insect or mite control purposes to a given area of plant life is, of course, dependent upon a variety of factors, such as the extent of vegetative surface to be covered, the severity of the insect infestation, the condition of the foliage treated, the temperature, the humidity, etc. In general, however, the application of about 0.1 to about 5.0 pounds of a benzimidazole represented by the above formula per acre of insect-infested plant life provides effective insecticidal action. The application to plant foliage to the point of run-off of aqueous compositions containing from about 0.01 to about 0.6 percent on a weight-volume basis of a benzimidazole effectively controls the insecticidal life thereon. Alternatively, a light but complete dusting of plant foliage with a dusting composition containing, by weight, about 0.1 to about 0.6 percent of the benzimidazole also gives effective insecticidal control.

The benzimidazoles of this invention can also be formulated so as to contain other compatible insecticidal agents. Among these agents are included rotenone; natural or synthetic esters of chrysanthemic acid and its relatives including pyrethrin and allethrin; chlorinated hydrocarbons, including BHC, lindane, chlordane, heptachlor, toxaphene, aldrin, dieldrin, endrin, DDT, TDE, and methoxychlor; organic phosphates, including TEPP, phosphamiden, demeton, malathion, ethion, dimethoate, mecarbam, methyl parathion, parathion, O-2,4-dichlorophenyl-O-methyl isopropylphosphoramidothioate, ronnel, O-4-tert-butyl-2-chlorophenyl-O-methyl methylphosphoramidate, tepa, metepa, diazinon and meta systox; sulfites, including 2-(p-tert-butylphenoxy)-1-methylethyl-2-chloroethyl sulfite; and carbamates, including 4-dimethylamino-3,5-xylyl methylcarbamate and carbaryl.

Illustrative formulations useful in the process of this invention include the following

I. WETTABLE POWDER 25 percent 2,6-bis(trifluoromethyl)-4-nitrobenzimidazole,
70.5 percent Kaolin
3 percent alkylarylpolyether alcohol,
1.5 percent sodium lignin sulfonate

II. GRANULES

An impregnating solution is prepared containing six parts of 2,6-bis(trifluoromethyl)-4-nitrobenzimidazole mixed with four parts of methyl cellosolve. Seventeen and two tenths grams of this solution is sprayed onto 82.8 g. of diatomaceous earth and the mixture is compressed into granules containing 10 percent of active ingredient.

III. GRANULES

An impregnating solution is prepared containing six parts of the sodium salt of 2,6-bis(trifluoromethyl)-4-nitrobenzimidazole and four parts tap water. Seventeen and two tenths grams of the solution is sprayed onto diatomaceous earth as before and the sprayed material compressed into granules containing 10 percent active ingredient.

IV. DUST

One part 2,6-bis(trifluoromethyl)-4-nitrobenzimidazole is mixed with 99 parts of talc after both ingredients have been ground finely enough to pass through a 325 mesh sieve.

Benzimidazoles represented by Formula I above have an extremely broad insecticidal and miticidal spectrum. The compounds are particularly active against insects belonging to the order Coleoptera—beetles—including both larval and adult forms of Mexican bean beetle, boll weevil, corn rootworm, cereal leaf beetle, flea beetles, borers, zebra caterpillar, milkweed beetle, Colorado potato beetle, grain beetles, alfalfa weevil, carpet beetle, confused flour beetle, elm leaf beetle, striped cucumber beetle, yellow meal worm, powder post beetle, wireworms, rice weevil, rose beetle, picnic beetle, asparagus beetle, bean leaf beetle, plum curculio and white grubs. 2-Fluoroalkyl-6-fluoromethyl-4-nitrobenzimidazoles and their N-derivatives are also extremely active against insects of the order Hemiptera, including melon aphid, tarnished plant bug, tulip tree aphid, meadow spittle bug, rose aphid, white fly, grain aphid, apple aphid, sour gum aphid, corn leaf aphid, pea aphid, mealybugs, scales, leafhoppers, citrus aphid, squash bug, green leafhopper, buffalo tree hopper, spotted alfalfa aphid, green peach aphid and bean aphid. The compounds also have an extremely high activity against mites including red spider mites (at application rates of 10 ppm or less), clover mites, rust mites, citrus mites, two-spotted spider mites and fowl mites. These compounds are also active against insects of the orders Diptera, such as house fly, yellow fever mosquito, stable fly, horn fly, cabbage maggot, and carrot rust fly; and Lepidoptera, such as Southern armyworm, walnut caterpillar, coddling moth, cutworm, clothes moth, Indianmeal moth, leafrollers, corn ear worm, European corn borer, variegated cutworm, imported cabbage worm, cabbage looper, cotton bollworm, bagworm, sod webworm, Eastern tent caterpillar, fall webworm, tussock moth and fall armyworm. Finally, the compounds have shown activity against roaches and grasshoppers of the order Orthoptera at rates comparable to those employed with presently marketed insecticides for the purpose of roach control.

The insecticidal and miticidal activity of the compounds of this invention is illustrated by the following tests against representative insects and mites.

TEST METHODS

Mexican Bean Beetle

*Epilachna varivestis* (Coleoptera)

Cuttings of four six-day old Bountiful snap bean plants containing two leaves with approximately 5 square inches of leaf surface, are placed in water. The leaves are sprayed to wetting with about 5–10 ml. of a formulation containing a pre-determined level of the test compound. Half of the formulation is sprayed on the top surface and half on the bottom surface of the leaf using a DeVilbiss atomizer at 10 psi held at a distance of about 18 inches from the leaf. After the leaves have dried, they are cut from the stem and placed separately in petri dishes. Ten third instar, nonmolting Mexican bean beetle larvae grown on Bountiful snap beans are placed on each leaf. Controls consist of two leaves sprayed with 5 ml. of a 500 ppm malathion formulation (reference standard), two leaves sprayed with the formulation without the active ingredient and two leaves are held as untreated controls. After 48 hours, a mortality count is made and the amount of feeding noted. Moribund larvae are counted as dead. The following rating scale is used:

| Percent dead | Rating |
|---|---|
| 0–10 | 0 |
| 11–20 | 1 |
| 21–30 | 2 |
| 31–40 | 3 |
| 41–50 | 4 |
| 51–60 | 5 |
| 61–70 | 6 |
| 71–80 | 7 |
| 81–90 | 8 |
| 91–100 | 9 |

Southern Armyworm

*Prodenia eridania* (Lepidoptera)

Ten uniform Southern armyworm larvae about 1–1.5 cm. in length, grown on Henderson lima beans, are placed on excized bean leaves in petri dishes. The bean leaves are obtained and sprayed with the insecticide in the same way as are the snap bean leaves in the Mexican bean beetle test. The reference standards in this instance are leaves sprayed with 5 ml. 100 ppm DDT solution. Mortality counts are made 48 hours after spraying and again moribund larvae are counted as dead. Missing larvae which have probably been eaten are considered alive. The same rating scale is used as in the Mexican bean beetle test.

Melon Aphid

*Aphis gossypii* (Hemiptera)

Four blue hubbard squash seeds are planted per container in vermiculite and the containers watered from the bottom. After 6 days, the two weakest plants are cut off and one cotyledon and the primary leaves are removed from each of the two remaining plants. The remaining cotyledon is infested with 100 melon aphids from a stock colony by pinning the cotyledon against an aphid-infested squash cotyledon from the colony and allowing the aphids to transfer. After transfer, the colony leaf is removed. Forty-eight hours later, the infested leaves are sprayed to wetting with formulations containing graded amounts of the insecticide using a DeVilbiss atomizer at 10 psi held at 12–15 inches from the plant. Controls consist of two infested, unsprayed squash plants and two infested plants sprayed to wetting with a formulation containing 100 ppm malathion as a reference standard. The mortality is estimated 24 hours after spraying by observation using a 10 power dissecting microscope. The same rating scale is used as before.

Two-spotted Spider Mite

*Tetranychus urticae* (Acarina)

The procedure in this test is the same as that in the previous aphid test, except that about 100 two-spotted spider mites from a stock colony raised on squash plants are transferred to a cut squash cotyledon. The mortality is estimated 48 hours after spraying. The same rating scale is used.

Milkweed Bug

*Oncopeltis fasciatus* (Hemiptera)

Ten adult milkweed bugs are chilled and placed in a test cage. The cages containing the bugs are sprayed with 5 ml. of a test formulation containing a pre-determined amount of the insecticide, using a DeVilbiss atomizer at 10 psi held 33 inches from the top of the cage. After the cage has been allowed to dry, the bugs are fed and watered for 48 hours. A formulation containing 500 ppm of malathion is used as a reference standard and two unsprayed cages are kept as controls. Mortality counts are made 48 hours after spraying. Moribund adults are considered dead. The same rating scale is employed as before.

House Fly

*Musca domestica* (Diptera)

A. Contact

Rearing cages containing four-day old adult house flies are chilled at 35°–40° F. for about 1 hour. One hundred flies are transferred from the rearing cage to each test cage using a small scoop. The caged flies are kept for 1–2 hours at 70°–80° F. The cages are sprayed in the same manner as described for the milkweed bug with 5 ml. of the test formulation. Two unsprayed cages are held as controls and two cages are sprayed with a 50 ppm DDT formulation as a reference standard. Mortality counts are made 24 hours after spraying. All flies that do not fly or do not walk up from the bottom of the cage are considered moribund. The same rating scale is employed as heretofore.

B. Stomach

Ten chilled house flies are taken from the rearing cage and placed in a covered petri dish. Sugar cubes treated with 0.2 ml. of a formulation containing a specified level of the insecticide are placed in the petri dish one hour after the flies have been removed from the chill room. Controls consist of sugar cubes treated with 0.2 ml. of deionized water and cubes treated with 0.2 ml. of a formulation containing 500 ppm of malathion. Mortality counts are made 24 hours later. The same rating scale is used as before.

Oriental Cockroach

*Blatta orientalis* (Orthoptera)

A rearing pan of late instar (3–4 months old) roaches is placed in a cold room for about 1 hour. Ten nymphs are taken from the pan and placed in each cage and the caged insects are kept at 70°–80° F. for 1 hour. The test cages are then sprayed in the manner indicated above in the milkweed bug test using 5 ml. of a formulation containing a specified amount of the insecticide. The test cages are held for 72 hours during which time the cockroaches are neither fed nor watered. Controls consist of 2 unsprayed cages, two cages sprayed with the formulation alone and 2 cages with a formulation containing 1000 ppm of heptachlor. Mortality counts are made 24 hours after spraying by shaking the cages lightly. All cockroaches remaining in the bottom are counted as dead.

Boll Weevil

*Anthonomus grandis* (Coleoptera)

The procedure is identical to that employed for the Mexican bean beetle and the Southern armyworm, except that 10 adult boll weevils are placed on cotton leaves that have been dipped into formulations of the test compounds. The same rating scale is used.

Test Results

The following tables show the effect of the selected compounds of this invention against the above insect and mite species. In each of the following tables, the compound under test as indicated by a letter according to the following chart:

A  2,6-bis(trifluoromethyl)-4-nitrobenzimidazole
B  2,6-bis(trifluoromethyl)-4-nitrobenzimidazole, sodium salt
C  Mixture of benzyl 2,6-bis(trifluoromethyl)-4-nitro-1-benzimidazolecarboxylate and benzyl 2,5-bis(trifluoromethyl)-7-nitro-1-benzimidazolecarboxylate
D  Mixture of methyl 2,6-bis(trifluoromethyl)-4-nitro-1-benzimidazolecarboxylate and methyl 2,5-bis(trifluoromethyl)-7-nitro-1-benzimidazolecarboxylate
E  n-hexyl 2,6-bis(trifluoromethyl)-4-nitro-1-benzimidazolecarboxylate
F  2,6-bis(trifluoromethyl)-4-nitro-1-phenylsulfonyl-benzimidazole
G  ethyl 2,6-bis(trifluoromethyl)-4-nitro-1-benzimidazolecarboxylate
H  Mixture of phenyl 2,6-bis(trifluoromethyl)-4-nitro-1-benzimidazolecarboxylate and phenyl 2,5-bis(trifluoromethyl)-1-benzimidazolecarboxylate
I  isopropyl 2,6-bis(trifluoromethyl)-4-nitro-1-benzimidazolecarboxylate
K  allyl 2,6-bis(trifluoromethyl)-4-nitro-1-benzimidazolecarboxylate
L  2-chlorodifluoromethyl-4-nitro-6-trifluoromethyl-benzimidazole
M  2-trifluoromethyl-4-nitro-6-difluoromethylbenzimidazole
N  p-nitrophenyl-4-nitro-2,6-bis(trifluoromethyl)-1-benzimidazolecarboxylate
O  Mixture of N-ethyl-4-nitro-2,6-bis(trifluoromethyl)thio-1-benzimidazolecarboxanilide and N-ethyl-nitro-2,5-bis(trifluoromethyl)thio-1-benzimidazolecarboxanilide
P  Mixture of N,N-dimethyl-4-nitro-2,6-bis(trifluoromethyl)thio-1-benzimidazolecarboxamide and N,N-dimethyl-7-nitro-2,5-bis(trifluoromethyl)thio-1-benzimidazolecarboxamide
Q  2-difluoromethyl-4-nitro-6-trifluoromethylbenzimidazole
R  Mixture of 7-nitro-1-piperidinothionocarbonyl-2,5-bis(trifluoromethyl)benzimidazole and 4-nitro-1-piperidinothionocarbonyl-2,6-bis(trifluoromethyl)-benzimidazole
S  N,N-diethyl-4-nitro-2,6-bis(trifluoromethyl)thio-1-benzimidazolecarboxamide
T  6-difluoromethyl-4-nitro-2-trifluoromethylbenzimidazole
U  ethyl 4-nitro-2,6-bis(trifluoromethyl)benzimidazolecarboxylate
V  4-nitro-6-trifluoromethyl-2-chlorodifluoromethyl-benzimidazole The symbols C, D, H, O, P and R are used in the following tables to designate not only a mixture of isomers as above, but also a single isomer if same had been separated and tested separately.

In the following tables, the insect or mite used as the test organism is indicated in the heading. Column 1 of each table gives the code letter for the test compound and columns 2 etc. the average rating using the above rating scale from 0–9 at decreasing concentrations beginning at 1000 ppm to the point where the insecticide shows virtually no activity. Included in each test are one or more standard insecticides.

Table 1

| Compound | Mexican Bean Beetle Test Ratings in ppm | | | | | | | |
|---|---|---|---|---|---|---|---|---|
| | 1000 | 500 | 250 | 100 | 50 | 25 | 10 | 5 |
| A | 9 | 9 | 9 | 9 | 9 | 9 | 9 | 7 |
| B | 9 | 9 | 9 | 9 | 8 | 6 | 7 | 2 |
| C | 9 | 9 | 9 | 9 | 9 | — | — | — |
| D | 9 | 9 | 9 | 9 | 9 | 9 | 9 | 0 |
| E | 9 | 9 | 9 | 9 | 5 | 7 | 7.5 | 2.5 |
| F | 9 | 9 | 9 | 9 | 9 | 8 | 7 | 0 |
| G | 9 | — | — | — | — | — | — | — |
| H | 9 | 9 | 9 | 9 | 7 | 3 | 4 | — |
| I | 9 | 9 | 9 | 9 | 9 | 6.5 | 8 | 0 |
| K | 9 | — | — | — | — | — | — | — |
| L | — | 9 | 9 | 9 | 8.5 | 9 | 7 | 4 |
| M | 9 | 7.5 | 9 | 5.5 | 1.5 | — | — | — |
| N | 9 | 9 | 9 | 9 | 9 | 9 | 4 | — |
| O | 9 | 9 | 9 | 6.5 | 5.5 | 6 | 1.5 | — |
| P | 9 | 8.5 | 7.5 | 7 | 4.5 | 0 | 0 | — |
| Malathion | | 7–8 | | | | | | |

TABLE 2

| Compound | Southern Armyworm Test Ratings in ppm | | | |
|---|---|---|---|---|
| | 1000 | 500 | 250 | 100 |
| A | 9 | 6 | 3 | — |
| B | 9 | 4 | 3 | 0 |
| C | 7 | 6 | — | 2 |
| D | 1 | — | — | — |
| E | 7.5 | 5.0 | 2 | 0 |
| F | 4 | 0 | — | — |
| G | 6 | — | — | — |
| H | 1 | 1 | 1 | — |
| I | 8 | 6 | 4 | 0 |
| K | 8 | — | — | — |
| L | — | 1.5 | — | — |
| M | 8 | .5 | — | — |
| P | 3.5 | 0 | 0 | — |
| DDT | | | | 7 |

TABLE 3

| Compound | Melon Aphid Test Ratings in ppm | | | | | | | |
|---|---|---|---|---|---|---|---|---|
| | 1000 | 500 | 250 | 100 | 50 | 25 | 10 | 5 |
| A | 9 | 8 | 8 | 7 | 5 | 1 | 0 | — |
| B | 9 | 9 | 8 | 7 | 7 | 8 | 9 | 0 |
| C | 8 | 9 | 5 | 0 | — | — | — | — |
| D | 9 | 9 | 9 | 4 | 2 | 0 | — | — |
| E | 9 | 9 | 9 | 9.5 | 8 | 7 | 7 | 1.5 |
| F | 9 | 9 | 9 | 8 | 2 | 0 | — | — |
| G | 9 | — | — | — | — | — | — | — |
| H | 6 | 8 | 7 | 8 | 4 | 0 | — | — |
| I | 9 | 9 | 6.5 | 8 | 8.5 | 6 | 3 | 0 |
| K | 9 | — | — | — | — | — | — | — |
| L | — | 9 | 9 | 9 | 6 | 5.5 | 0 | — |
| M | 9 | 9 | 9 | 7 | 0 | — | — | — |
| N | 9 | 9 | 7.5 | 1 | 0 | — | — | — |
| P | 4.5 | 7.5 | 7 | 4 | — | 1.5 | 0 | — |
| Malathion | | | | | 8 | | | |

TABLE 4

| Compound | Two-spotted Spider Mite Ratings in ppm | | | | | | | | |
|---|---|---|---|---|---|---|---|---|---|
| | 1000 | 500 | 250 | 100 | 50 | 25 | 10 | 5 | 2.5 | 1 |
| A | 9 | 9 | 9 | 9 | 9 | 8 | 8 | 5 | — | — |
| B | 9 | 9 | 9 | 9 | 9 | 8.5 | 6 | 5 | 1 | — |
| C | 9 | 9 | 9 | 9 | 9 | 7 | 8 | — | — | — |
| D | 9 | 9 | 9 | 6 | 9 | 4 | 3 | — | — | — |
| E | 9 | 9 | 9 | 9 | 8 | 9 | 8.5 | .5 | — | — |
| F | 9 | 9 | 9 | 9 | 9 | 9 | 6.8 | 7.5 | — | 6.3 |
| G | 9 | — | — | — | — | — | — | — | — | — |
| H | 9 | 9 | 9 | 9 | 8 | 2 | 5.5 | — | — | 0 |
| I | 9 | 9 | 9 | 9 | 9 | 8 | 8 | 0 | — | 0 |
| K | 9 | — | — | — | — | — | — | — | — | — |
| L | — | 9 | 9 | 9 | 9 | 9 | 8 | 7.5 | — | 0 |
| M | 9 | 9 | 8.5 | 6.5 | 1 | — | — | — | — | — |
| N | 9 | 8.5 | 8 | 8 | 8 | 9 | 6 | 1.5 | — | 2.5 |
| O | 5 | — | — | — | — | — | — | — | — | — |

TABLE 4-continued

Two-spotted Spider Mite Ratings in ppm

| Compound | 1000 | 500 | 250 | 100 | 50 | 25 | 10 | 5 | 2.5 | 1 |
|---|---|---|---|---|---|---|---|---|---|---|
| P | 9 | 9 | 8.5 | 7.5 | 7.0 | 6 | 4 | 4 | — | 3 |
| Aramite | | | | | 7-9 | | | | | |

TABLE 5

Milkweed Bug Test Ratings in ppm

| Compound | 1000 | 500 | 250 | 100 | 50 | 25 | 10 |
|---|---|---|---|---|---|---|---|
| A | 9 | 9 | 9 | 7 | 4 | 4 | 5 |
| B | 9 | 9 | 9 | 2 | 2 | 1 | — |
| C | 9 | 8.5 | 8 | — | 7 | 0 | 0 |
| D | 9 | 9 | 9 | 8 | — | 5 | — |
| E | 9 | 9 | 8 | 4 | 1.5 | 6.5 | .5 |
| F | 9 | 9 | 9 | 7.5 | 6 | 0 | 0 |
| G | 9 | — | — | — | — | — | — |
| H | 9 | 9 | 1 | — | — | — | — |
| I | 8 | 9 | 9 | 8 | 1 | 0 | 0 |
| K | 9 | — | — | — | — | — | — |
| L | — | 9 | 9 | 4.5 | 6 | 0 | 0 |
| M | 9 | 9 | 9 | 3.5 | .5 | — | — |
| N | 8 | 9 | 9 | 7 | 1 | 0 | 0 |
| O | 1 | — | — | — | — | — | — |
| P | 2 | 4 | 4 | 4.5 | 3.5 | 0 | 0 |
| Malathion | | 7-8 | | | | | |

TABLE 6

Housefly (Contact) Test Ratings in ppm

| Compound | 1000 | 500 | 250 | 100 | 50 | 25 | 10 |
|---|---|---|---|---|---|---|---|
| A | 9 | 9 | 9 | 9 | 8 | 8 | 4 |
| B | 9 | 9 | 9 | 9 | 8.5 | 3 | 3 |
| C | 9 | 9 | 9 | 5.5 | 4 | 0 | 0 |
| D | 9 | 9 | 9 | 9 | 9 | 0 | 0 |
| E | 9 | 9 | 9 | 4 | 1.5 | 8 | 4.5 |
| F | 9 | 9 | 9 | 9 | 9 | 0 | 0 |
| G | 9 | — | — | — | — | — | — |
| H | 9 | 9 | 9 | 9 | 7 | 7 | 3 |
| I | 9 | 9 | 9 | 9 | 9 | 6 | 5 |
| K | 9 | — | — | — | — | — | — |
| L | — | 9 | 9 | 9 | 9 | 9 | 1 |
| M | 9 | 9 | 9 | 9 | 9 | 9 | 8.5 |
| N | 9 | 9 | 9 | 9 | 9 | 8 | 1 |
| O | 7 | 9 | 9 | 9 | 8 | 8.5 | 6.5 |
| P | 9 | 9 | 9 | 9 | 9 | 8.5 | 4.0 |
| DDT | | | | | 6-8 | | |

TABLE 7

Housefly (Stomach) Test Ratings in ppm

| Compound | 1000 | 500 | 250 | 100 | 50 | 25 | 10 | 5 |
|---|---|---|---|---|---|---|---|---|
| A | 9 | 9 | 9 | 7 | 2 | — | — | — |
| B | 9 | 9 | 9 | 9 | 4 | 1 | — | — |
| C | 9 | 4 | 0 | — | — | — | — | — |
| D | 8.5 | 5.5 | 2 | — | — | — | — | — |
| E | 9 | 9 | 8 | 7 | 1 | — | — | — |
| F | 9 | 9 | 1 | — | — | — | — | — |
| G | 0 | — | — | — | — | — | — | — |
| H | 9 | — | — | 0 | — | — | — | — |
| I | 9 | — | 9 | 9 | 6 | 0 | — | — |
| K | 9 | — | — | — | — | — | — | — |
| L | — | 9 | 9 | 7 | .5 | — | — | — |
| M | 9 | — | — | 5.5 | 0 | 0 | 0 | — |
| N | 9 | 9 | 9 | 0 | 0 | — | — | — |
| O | 1 | — | — | — | — | — | — | — |
| P | — | 9 | 7 | 3 | 0 | — | — | — |
| Malathion | | 6-7 | | | | | | |

TABLE 8

Oriental Roach Test Rating in ppm

| Compound | 1000 | 500 | 250 | 100 | 50 | 25 | 10 |
|---|---|---|---|---|---|---|---|
| A | 7 | 4 | 5 | 0 | — | — | — |
| B | 9 | 6 | 2 | 3.5 | 1 | .5 | 0 |
| C | 9 | 1.5 | .5 | 3 | 1.5 | — | — |
| D | 9 | 9 | 5.5 | 0 | 0 | — | — |
| E | 9 | 8.5 | 2 | 2 | 0 | — | — |
| F | 8 | 4 | 3 | 0 | 0 | — | — |
| G | 5.5 | — | — | — | — | — | — |
| H | 5 | 6.5 | 7 | .5 | 0 | — | — |
| I | 9 | 6.5 | 5.5 | 1.5 | 0 | — | — |
| K | 9 | — | — | — | — | — | — |
| L | — | 5.5 | 1 | 0 | 0 | — | — |
| M | 9 | 1.5 | 0 | — | — | — | — |
| N | 5.5 | 4.5 | 0 | 0 | 0 | — | — |
| O | 0 | — | — | — | — | — | — |
| P | 8 | 9 | 5.5 | 2.5 | 0 | — | — |
| Heptachlor | 8-9 | | | | | | |

TABLE 9

Boll Weevil Test Ratings in ppm

| Compound | 1000 | 500 | 250 | 100 | 50 | 25 | 10 | 5 |
|---|---|---|---|---|---|---|---|---|
| A | 9 | 9 | 9 | 9 | 8.5 | 8.8 | 6.7 | 7.5 |
| B | 9 | 9 | 8.5 | 9 | 9 | 8.5 | 6 | 6 |
| C | 9 | 9 | 9 | 9 | 7 | 8.5 | 4.5 | — |
| D | 9 | 9 | 9 | 9 | 9 | 8.5 | 5.5 | 0 |
| E | 9 | 9 | 9 | 9 | 9 | 6.5 | 8 | 2 |
| F | 9 | 9 | 8.5 | 9 | 6.5 | 7.5 | 4 | — |
| G | 9 | — | — | — | — | — | — | — |
| H | 9 | 9 | 9 | 9 | 8 | 5.5 | 1 | — |
| I | 9 | 9 | 9 | 7.5 | 8.5 | 8.5 | 8 | 6 |
| K | 9 | — | — | — | — | — | — | — |
| L | — | 9 | 9 | 9 | 9 | 1.5 | .5 | — |
| M | 7.5 | 8.5 | 8.5 | 5 | 1.5 | — | — | — |
| N | 9 | — | — | — | — | 3.5 | 1.5 | — |
| O | 9 | 9 | 8.5 | 8 | 7.5 | 6.5 | 0 | — |
| P | 9 | 9 | 9 | 9 | 8 | 5 | 1.5 | — |
| Malathion | | 7-8 | | | | | | |

During two recent summers, insects or mites were collected in the field and one or more benzimidazoles coming within the scope of this invention were tested for their ability to kill these insects or mites. The test methods employed were as follows.

Insect Contact Poison Test

Infested plants are placed in 6 oz. prescription bottles filled with water to keep them from wilting. Cellucotton is wrapped around the plant stem and squeezed into the bottle neck to prevent the insects from drowning.

A DeVilbiss Special Atomizer (5004) is used at 10 psi to spray the test plant with different concentrations of compounds. The atomizer is held at arm's length to prevent blowing the insects off the host plant. After treating, the bottles are placed on a table covered with brown wrapping paper to catch the dead insects as they drop from the plant. The plants are spaced so the leaves or plants are not touching one another.

The results are read at 24, 48, and 72 hours when applicable. The rating scale is 0 to 9 where 0 = 0-10 percent and 9 = 91-100 percent mortality.

In a variation of the above test, 1 microliter of a test solution containing a predetermined number of micrograms of benzimidazole was applied directly to larvae or adult insects.

Insect Dipping Test

Insects are dipped into solutions of the test compounds, then placed on absorbent paper and gently rolled or patted until they are dry.

Then a leaf or a piece of the host plant is placed in a plastic petri dish (100 × 25 mm) and moist cellucotton is placed around the stem to keep the plant from wilting. The insects are then placed in the dish. Five or ten insects are used per replicate depending on the number available. There are two or more replicates per concentration and usually three concentrations per compound.

Mortality results are then taken at 24, 48 and 72 hours after treatment. The rating scale is 0 to 9, as before.

Larvae for the test are produced as described in Method Number G14:8–10.

Mosquito Larvae Test

*Aedes aegypti* larvae 5 days old are allowed to feed on fresh food for at least 3 hours previous to being placed on test. Larvae are then removed from the rearing pans by pouring on a 20 mesh screen, washing with deionized water, and pooling in a 6-inch white enameled sauce pan.

Twenty larvae are placed in a 1 oz. paper cup containing 25 ml. of deionized water.

Test chemicals are dissolved in a suitable solvent and pipetted under the surface of 225 ml. of deionized water in one pint wide-mouthed Mason jar test containers and stirred. A cup containing 20 larvae in 25 ml. of water is then added. This gives a final volume of 250 ml. and dilutes the chemical to 20 ppm.

Results are determined 48 hours later by counting the dead and moribund larvae. Dead larvae are those that do not move when the test container is tapped sharply with a pencil, or are obviously dead (discolored, bloated, shrunken) or are able to make only a few jerky motions of the body without actual locomotion. Moribund larvae are those that are capable of limited, or poorly coordinated, locomotion in a sluggish manner.

Live larvae respond normally and actively. The rating code is as follows:

| Number Larvae Dead and/or Moribund | Rating | % Dead |
|---|---|---|
| 0–2 | 0 | 0–10% |
| 3–4 | 1 | 15–20% |
| 5–6 | 2 | 25–30% |
| 7–8 | 3 | 35–40% |
| 9–10 | 4 | 45–50% |
| 11–12 | 5 | 55–60% |
| 13–14 | 6 | 65–70% |
| 15–16 | 7 | 75–80% |
| 17–18 | 8 | 85–90% |
| 19–20 | 9 | 95–100% |
| 20 Dead | 94+ | 100% |

Insect Stomach Poison Test

Leaves from the infested plant are treated with different concentrations of the test compounds, either by spraying with a DeVilbiss Special Atomizer (5004) at 10 psi or by dipping the leaves in solutions containing the compound. The leaves are then allowed to air dry.

After the leaves have dryed, they are placed in plastic petri dishes (100 × 25 mm), then the insects are counted out into each dish, five or ten insects per dish depending on the number of insects available. There are one or two replicates and usually two or three rates with each compound. Mortality results are taken at 24, 48 and 72 hours. The rating scale is 0 to 9.

Miticide Test

Citrus cuttings were obtained and prepared for testing within 24 hours prior to inoculation with citrus rust mites. To prepare the cuttings, terminals of branches 12 to 14 inches in length were cut from temple orange trees, immediately placed in tap water and taken into the laboratory. Uniform hardwood cuttings, 3 to 4 inches in length, were cut from the branches, all but one hardened leaf was removed from the cuttings, and the remaining leaf was wiped clean with a cotton pad soaked in 10% ethanol solution. Each cutting was immediately placed in tap water in a test tube with the closed leaf extending out of the test tube. Then, a ring of melted lanolin was applied around the petiole to prevent migration of mites from the leaf. One cutting was used for each replicate.

When the leaves were dry immediately after cleaning, citrus rust mites were transferred to the test leaves by cutting a heavily infested colony leaf (from a source colony maintained on citrus seedlings) into 20 to 22 sections (approximately 0.25 by 0.5 inches in size) and using forceps to place 1 section on each leaf cutting. As the section became desiccated the mites moved to the whole leaf and in 20 hours the sections were removed from the leaves for treatment application.

Treatments were applied within 24 hours after inoculation by removing the cuttings from the test tube and submerging the leaves in the treatment solution for 5 seconds by hand and immediately returning the cutting to the test tube.

Each 5 mg. sample of technical compound pre-weighed at Greenfield was dissolved in 2.5 ml. of acetone and diluted with 247.5 ml. of water containing a combination of surfactants to provide 250 ml. of solution which was then used to treat at the rate of 220 ppm. Next, the 250 mls. of treatment solution was diluted with 250 ml. of surfactant-containing water to provide 500 mls. of solution which was then used to treat at the rate of 10 ppm. A 5 ppm. solution was obtained in similar fashion.

The treated cuttings were stored in the greenhouse for 24 hours before evaluation under a binocular disecting microscope in the laboratory. In evaluating the results of the miticide test, each treated cutting was removed from the test tube, observed for live and dead mites at 14 × magnification, and returned immediately to the test tube. A scale of 0–9 was used as before.

The test employing two-spotted spider mites was conducted in similar fashion except that the mites were maintained on squash seedlings or squash cuttings.

The compounds under test are given in the following list along with an alphabetical designation, the alphabetical designation being used in the insecticidal or miticidal test tables which follow.

Field Trials (Second Summer)

Using the above methods, field trials were carried out against species of 5 orders of insects. The results, which are summarized in the following tables, give the average mortality for the particular insect with a given benzimidazole for each concentration employed. A line in the table indicates that the insecticide was not tested at the particular concentration. These tables contain all results obtained during the summer trials.

| | | AVERAGE MORTALITY | | | |
|---|---|---|---|---|---|
| | | Hemiptera | | | Stomach |
| Compound | ppm | 100 | 50 | 25 | 10 |
| Aphids - Apple | | | | | |
| E | | 7 | 5 | 5 | — |

-continued

|  | | 750 | 500 | 250 | 125 |
|---|---|---|---|---|---|
| | U | 6 | 4 | 2 | — |
| | I | 9 | 5 | 1 | — |
| | A | 4 | 4 | 1 | — |
| | V | 4 | 1 | 1 | — |
| Aphids - Sour Gum | | | | | |
| | E | 5 | 3 | 1 | — |
| | U | 9 | 7 | 9 | — |
| | A | 9 | 9 | 7 | — |
| | V | 9 | 7 | 7 | — |
| Aphids - Tulip Tree | | | | | |
| | E | 8 | 6 | 6 | — |
| | U | 9 | 8 | 6 | — |
| | I | 5 | 5 | 5 | — |
| | A | 8 | 5 | 8 | — |
| | V | 5 | 1 | 1 | — |
| Meadow Spittlebug | | | | | |
| | I | — | 3 | 5 | 2 |
| | U | 0 | 3 | 5 | 5 |
| | F | — | 7 | 1 | 0 |
| | V | 5 | 1 | 0 | — |
| | E | 1 | 3 | 2 | 1 |
| | D | 5 | — | — | — |
| | A | — | 1 | 0 | 2 |
| | N | — | 0 | 1 | 1 |
| Tarnished Plant Bug Adults | | | | | |
| | F | — | 2 | 4 | 4 |
| | D | — | 7 | — | 3 |
| | N | — | 3 | 3 | 3 |
| | I | — | 2 | 4 | 3 |
| | V | — | 5 | 4 | 0 |
| | U | — | 6 | 1 | 0 |
| | D | — | 4 | 3 | 0 |
| | A | — | 2 | 1 | 3 |
| | E | — | 3 | 2 | 1 |
| | S | — | — | 5 | — |
| Unidentified Green Leafhopper | | | | | |
| | U | — | 9 | 7 | 3 |
| | E | — | 7 | 7 | 4 |
| | I | — | 7 | 6 | 2 |
| | D | — | 6 | 4 | 5 |
| | A | — | 6 | 2 | 4 |
| | H | — | 9 | 1 | 0 |
| | F | — | 7 | 1 | 1 |
| | N | — | 3 | 1 | 0 |
| | S | — | 0 | 0 | 3 |

| | | | Contact | | |
|---|---|---|---|---|---|
| Compound | ppm | 750 | 500 | 250 | 125 |
| Squash Bug Adults | | | | | |
| | A | 9 | 9 | 6 | 0 |
| | U | 7 | 7 | 5 | 5 |
| | V | 9 | 6 | 6 | 0 |
| | N | 8 | 5 | 6 | 1 |
| | F | 9 | 7 | 4 | 0 |
| | H | 8 | 6 | 2 | 2 |
| | E | 6 | 3 | 2 | 0 |
| | D | 3 | 2 | 0 | 0 |
| | I | 0 | 0 | 1 | 3 |

Diptera

| | | | | | Dip Test | |
|---|---|---|---|---|---|---|
| Compound | ppm | 0.1 | 0.05 | 0.025 | | 0.010 |
| Mosquito Larvae | | | | | | |
| | S | 9 | 5 | 5 | | 4 |
| | E | 8 | 1 | 0 | | 0 |
| | D | 4 | 0 | 0 | | — |
| | F | 9 | 8 | 5 | | 8 |

Orthoptera

| | | Contact | | | | | Stomach |
|---|---|---|---|---|---|---|---|
| Compound | ppm | 50 | 25 | 10 | 50 | 25 | 10 |
| Red-Legged Grasshopper Adults | | | | | | | |
| | U | 9 | 9 | — | — | — | — |
| | C | 9 | 9 | — | — | — | — |
| | V | 9 | 7 | — | — | — | — |
| | E | 7 | 8 | 3 | — | — | — |
| | A | 4 | 4 | 3 | 6 | 4 | 0 |
| | I | 5 | 3 | 2 | 4 | 4 | 0 |
| | Q | 5 | 4 | 0 | 5 | 1 | 1 |
| | H | 7 | 1 | — | — | — | — |

Lepidoptera

| | | | | | | Contact | | | | |
|---|---|---|---|---|---|---|---|---|---|---|
| Compound | ppm | 1500 | 1000 | 750 | 500 | 250 | 125 | 100 | 62.5 | 50 | 25 |
| Walnut Caterpillar | | | | | | | | | | | |
| | A | — | — | — | — | 7 | — | 1 | — | 1 | 1 |
| | I | — | — | — | — | 3 | — | 2 | — | 1 | 0 |
| Fall Webworm | | | | | | | | | | | |
| | A | —7 | 9 | 3 | 5 | 3 | — | — | — | — | — |
| Eastern Tent Caterpillar | | | | | | | | | | | |
| | A | — | 9 | — | 5 | 5 | — | 3 | — | 0 | — |
| | I | — | 5 | — | 6 | 3 | — | 1 | — | 0 | — |

-continued

| | | | | | | | | | | |
|---|---|---|---|---|---|---|---|---|---|---|
| Corn Earworm | | | | | | | | | | |
| A | — | — | 1 | 0 | 0 | 0 | — | 0 | — | — |
| Armyworm, *P. Unipuncta* | | | | | | | | | | |
| A | — | — | — | 3 | 1 | 0 | — | — | — | — |
| I | — | — | — | 0 | 0 | 0 | — | — | — | — |
| Bagworms | | | | | | | | | | |
| I | 0 | 1 | 2 | 5 | 4 | 1 | — | — | — | — |
| A | 0 | 0 | 1 | 4 | 4 | 0 | — | — | — | — |
| Imported Cabbage Worm | | | | | | | | | | |
| A | — | — | 7 | 3 | 4 | 3 | — | — | — | — |

Lepidoptera
Stomach

| Compound ppm | 5000 | 2500 | 1500 | 1000 | 750 | 500 | 250 | 125 | 100 | 50 |
|---|---|---|---|---|---|---|---|---|---|---|
| Walnut Caterpillar | | | | | | | | | | |
| A | — | — | — | — | — | — | 3 | — | 3 | 1 |
| I | — | — | — | — | — | — | 2 | — | 1 | 0 |
| Fall Webworm | | | | | | | | | | |
| A | — | — | — | 0 | 0 | 0 | 9 | — | — | — |
| Eastern Tent Caterpillar | | | | | | | | | | |
| A | — | — | — | 0 | — | 0 | 0 | — | — | — |
| I | — | — | — | 0 | — | 0 | 0 | — | — | — |
| Armyworm, *P. Unipuncta* | | | | | | | | | | |
| A | — | — | — | — | — | 9 | 9 | 9 | — | — |
| I | — | — | — | — | — | 2 | 4 | 2 | — | — |
| Bagworms | | | | | | | | | | |
| I | 1 | 1 | 0 | 1 | 0 | 1 | — | — | — | — |
| A | 1 | 0 | 1 | 0 | 0 | 1 | — | — | — | — |

Lepidoptera
Topical

| Compound µg/µl | 1.2 | 0.6 | 0.3 |
|---|---|---|---|
| Eastern Tent Caterpillar | | | |
| A | 3 | 1 | 3 |
| I | 2 | 1 | 0 |

Coleoptera
Contact

| Compound ppm | 1000 | 750 | 500 | 250 | 100 | 50 | 25 | 10 |
|---|---|---|---|---|---|---|---|---|
| Alfalfa Weevil Larvae | | | | | | | | |
| A | 5 | 3 | 3 | — | — | — | — | — |
| F | 8 | 8 | 8 | — | — | — | — | — |
| C | 6 | 4 | 4 | — | — | — | — | — |
| D | 7 | 6 | 2 | — | — | — | — | — |
| E | 4 | 2 | 4 | — | — | — | — | — |
| I | 1 | 2 | 1 | — | — | — | — | — |
| Bean Leaf Beetle | | | | | | | | |
| C | — | — | — | — | 7 | 2 | 0 | — |
| V | — | — | — | — | 6 | 4 | 0 | — |
| I | — | — | — | — | 4 | 0 | 0 | — |
| E | — | — | — | — | 8 | 0 | 0 | — |
| H | — | — | — | — | 4 | 0 | 0 | — |
| D | — | — | — | — | 1 | 0 | 0 | — |
| A | — | — | — | — | 0 | 0 | 0 | — |
| Q | — | — | — | — | 0 | 0 | 0 | — |
| Elm Leaf Beetle | | | | | | | | |
| A | 9 | — | 7 | 0 | — | — | — | — |
| I | 1 | — | 1 | 1 | — | — | — | — |
| Potato Flea Beetle Adults | | | | | | | | |
| F | — | — | — | — | — | 9 | 8 | 8 |
| A | — | — | — | 9 | 8 | 8 | 9 | 9 |
| I | — | — | — | 9 | 9 | 9 | 9 | 9 |
| E | — | — | — | 9 | 9 | 9 | 9 | 6 |
| S | — | — | — | — | — | 9 | 8 | 5 |
| Q | — | — | — | — | — | 8 | 6 | 3 |
| Southern Corn Rootworm Adults | | | | | | | | |
| A | — | — | — | — | 8 | 6 | 4 | — |
| E | — | — | — | — | 8 | 9 | 4 | — |
| D | — | — | — | — | 9 | 9 | 5 | — |
| D | — | — | — | — | 9 | 8 | 3 | — |
| U | — | — | — | — | 9 | 9 | 4 | — |
| V | — | — | — | — | 9 | 8 | 5 | — |
| R | — | — | — | — | 9 | 9 | 0 | — |
| B | — | — | — | — | 8 | 3 | 0 | — |
| F | — | — | — | — | 9 | 5 | 2 | — |
| C | — | — | — | — | 9 | 4 | 4 | — |
| H | — | — | — | — | 7 | 3 | 0 | — |
| N | — | — | — | — | 3 | 5 | 0 | — |
| Asparagus Beetles Larvae | | | | | | | | |
| A | — | — | — | — | — | 9 | 8 | 8 |
| Asparagus Beetles Adults | | | | | | | | |
| E | — | — | — | — | — | 9 | 8 | 7 |
| D | — | — | — | — | — | 9 | 8 | 3 |
| A | — | — | — | — | — | 8 | 7 | 7 |
| S | — | — | — | — | — | 5 | 8 | 0 |

Coleoptera
Stomach

| Compound ppm | 500 | 250 | 125 | 100 | 50 | 25 | 10 | 5 |
|---|---|---|---|---|---|---|---|---|
| Alfalfa Weevil Larvae | | | | | | | | |
| A | 7 | 7 | 7 | — | — | — | — | — |

-continued

| | | 7 | 2 | 1 | — | — | — | — | — |
|---|---|---|---|---|---|---|---|---|---|
| | F | 7 | 2 | 1 | — | — | — | — | — |
| | C | 6 | 5 | 3 | — | — | — | — | — |
| | D | 3 | 6 | 7 | — | — | — | — | — |
| | E | 3 | 4 | 1 | — | — | — | — | — |
| | I | 6 | 4 | 8 | — | — | — | — | — |
| Bean Leaf Beetle | | | | | | | | | |
| | C | — | — | — | — | 2 | 1 | 0 | — |
| | V | — | — | — | — | 0 | 1 | 1 | — |
| | I | — | — | — | — | 3 | 1 | 0 | — |
| | E | — | — | — | — | 0 | 1 | 0 | — |
| | H | — | — | — | — | 0 | 0 | 1 | — |
| | D | — | — | — | — | 1 | 0 | 1 | — |
| | A | — | — | — | — | 1 | 0 | 0 | — |
| | Q | — | — | — | — | 0 | 0 | 0 | — |
| Elm Leaf Beetle | | | | | | | | | |
| | A | 5 | 0 | 3 | — | — | — | — | — |
| | I | 3 | 0 | 0 | — | — | — | — | — |
| Potato Flea Beetle Adults | | | | | | | | | |
| | F | — | — | — | — | 9 | 9 | 9 | — |
| | A | — | — | — | 9 | 9 | 6 | 9 | — |
| | I | — | — | — | 9 | 8 | 8 | 6 | — |
| | E | — | — | — | 8 | 7 | 9 | 9 | — |
| | S | — | — | — | — | 9 | 7 | 3 | — |
| | Q | — | — | — | — | 5 | 1 | 1 | 0 |
| Striped Cucumber Beetle Adults | | | | | | | | | |
| | P | — | — | — | 9 | 5 | 4 | 5 | — |
| | C | — | — | — | 7 | 5 | 4 | 4 | — |
| | I | — | — | — | 9 | 6 | 3 | 2 | — |
| | H | — | — | — | 7 | 4 | 4 | 3 | — |
| | U | — | — | — | 9 | 4 | 1 | 2 | — |
| | D | — | — | — | 9 | 5 | 0 | 2 | — |
| | A | — | — | — | 5 | 6 | 3 | 1 | — |
| | E | — | — | — | 5 | 5 | 1 | 3 | — |
| | Q | — | — | — | 2 | 2 | 3 | 2 | — |
| | F | — | — | — | — | 3 | 3 | 0 | — |
| Southern Corn Rootworm Adults | | | | | | | | | |
| | A | — | — | — | 7 | 6 | 4 | — | — |
| | E | — | — | — | 5 | 5 | 5 | — | — |
| | D | — | — | — | 6 | 4 | 3 | — | — |
| | D | — | — | — | 6 | 4 | 4 | — | — |
| | U | — | — | — | 3 | 3 | 5 | — | — |
| | V | — | — | — | 6 | 4 | 1 | — | — |
| | R | — | — | — | 3 | 7 | 1 | — | — |
| | B | — | — | — | 9 | 5 | 4 | — | — |
| | F | — | — | — | 5 | 4 | 3 | — | — |
| | C | — | — | — | 4 | 2 | 1 | — | — |
| | H | — | — | — | 6 | 4 | 2 | — | — |
| | H | — | — | — | 8 | 2 | 3 | — | — |
| Asparagus Beetles Larvae | | | | | | | | | |
| | A | — | — | — | — | — | 7 | 7 | 3 |
| Asparagus Beetles Adults | | | | | | | | | |
| | E | — | — | — | — | — | 9 | 5 | 3 |
| | D | — | — | — | — | — | 9 | 5 | 5 |
| | A | — | — | — | — | — | 9 | 3 | 0 |
| | S | — | — | — | — | — | 9 | 7 | 7 |

| | | Coleoptera | | | Topical |
|---|---|---|---|---|---|
| Compound | μg/μl | 0.15 | 0.1 | 0.07 | 0.03 |
| Alfalfa Weevil Larvae | | | | | |
| | A | — | 1 | 2 | 2 |
| | F | — | 3 | 1 | 1 |
| | C | — | 4 | 1 | 2 |
| | D | — | 4 | 1 | 2 |
| | E | — | 4 | 2 | 2 |
| | I | — | 3 | 1 | 1 |
| Yellow Mealworm Larvae | | | | | |
| | V | 9 | — | 5 | 5 |
| | N | 7 | — | 3 | 1 |
| | U | 6 | — | 4 | 4 |
| | A | 5 | — | 5 | 3 |
| | Q | 7 | — | 4 | 1 |
| | H | 6 | — | 3 | 3 |
| | D | 6 | — | 3 | 2 |
| | K | 6 | — | 3 | 1 |
| | S | 4 | — | 4 | 2 |
| | F | 5 | — | 3 | 2 |
| | C | 5 | — | 4 | 1 |
| | R | 3 | — | 3 | 3 |
| | E | 4 | — | 3 | 2 |

ACUTE MORTALITY
Miticide Test
(Against the Two-Spotted Spider Mite (2-SSM)
and Citrus Rust Mite (CRM) as Foliar Sprays)

| | 100 ppm | | 50 ppm | | 25 ppm | | 12.5 ppm | | 6.25 ppm | |
|---|---|---|---|---|---|---|---|---|---|---|
| Compound | 2-SSM | CRM | 2-SSM | CRM | 2-SSM | CRM | 2-SSM | CRM | 2-SSM | CRM |
| I* | 8 | 9 | 8 | 9 | 8 | 9 | 2 | 7 | 3 | 5 |
| U** | 9 | 8 | 8 | 9 | 8 | 9 | 3 | 1 | 1 | 1 |

| -continued | | | | | | | | | | |
|---|---|---|---|---|---|---|---|---|---|---|
| E*** | 9 | 9 | 9 | 9 | 5 | 9 | 2 | 8 | 3 | 4 |

*CRM data collected after 24 hours
**CRM data collected after 72 hours
***CRM data collected after 48 hours

Field Trials (First Summer)

During the previous summer similar field trials were conducted employing the same tests as heretofore but with some additional species of insects not included in the later tests. The results listed below are for tests in which an insect mortality was established by a given application route and at a given concentration in a particular test. The same 0 – 9 scoring system is used as is the designation of compounds by alphabetical symbols.

| INSECT MORTALITY | | | | | |
|---|---|---|---|---|---|
| Coleoptera | | | | | |
| | | Topical | | | |
| Compound μg/μl | .0625 | .078125 | .15625 | .25 | .3125 |
| Boll Weevil | | | | | |
| A,K,H,F,B,P,C,D | 9 | | | | |
| E | | | 9 | | |
| Q | | | 5 | | |
| Mexican Bean Beetle | | | | | |
| A,K,F,D | | | | 9 | |
| E | 9 | | | | |
| Picnic Beetle | | | | | |
| D,C,A,K,Q,S,B,E,P | 9 | | | | |
| Confused Flour Beetle | | | | | |
| A,K,C,F, | 9 | | | | |
| Q | 7 | | | | |
| H | | | 9 | | |
| B,E | | | | | 9 |

| Coleoptera | | |
|---|---|---|
| | | Stomach |
| Compound ppm | 500 | 250 |
| Zebra Caterpillar | | |
| A | 7 | |
| E | 5 | |
| Picnic Beetle | | |
| A,S,E,D | | 9 |

| Coleoptera | | |
|---|---|---|
| | | Contact |
| Compound ppm | 250 | 125 |
| Picnic Beetle | | |
| S,D,A,E | 9 | |
| Milkweed Beetle | | |
| A,S,E,D | | 9 |

| Hemiptera | |
|---|---|
| | Contact |
| Compound ppm | 125 |
| Buffalo Tree Hopper | |
| A,K | 9 |

| Lepidoptera | | |
|---|---|---|
| | | Stomach |
| Compound ppm | 750 | 500 |
| Cabbage Looper | | |
| A | | 9 |
| Variegated Cutworm | | |
| A | | 5 |
| Tussock Moth | | |
| A | 9 | |
| E | 5 | |

| Lepidoptera | |
|---|---|
| | Contact |
| Compound ppm | 750 |
| Tussock Moth | |
| A | 9 |

| Orthoptera | |
|---|---|
| | Contact |

| -continued | | | |
|---|---|---|---|
| Compound ppm | 500 | 250 | 125 |
| Differential Grasshopper | | | |
| A,K | | | 9 |
| E | | 9 | |
| Meadow Grasshopper | | | |
| A,K,E | | | 9 |
| German Roach | | | |
| A | 8 | | |
| American Roach | | | |
| A | 9 | | |

Novel compounds represented by Formulas II and III above, which compounds form a second aspect of this invention, are prepared by reacting the sodium salt of a 2-fluoroalkyl-6-fluoromethyl-4-nitrobenzimidazole with an acid chloride according to the following equation:

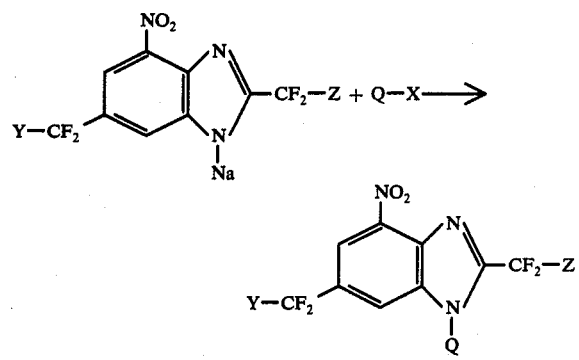

wherein Y, Z, Q, R', R'', R''', R'''' have the same meaning as above, and X is a halogen having an atomic number below 36. (The preparation of the N-derivatives of a 2-fluoroalkyl-6-fluoromethyl-4-nitrobenzimidazole has been illustrated with respect to only the 6-fluoromethyl-4-nitro isomer, but it will be understood from the previous discussion that the reaction also produces the 5-fluoromethyl-7-nitro isomer, and that the sodium salt of the 2-fluoroalkyl-6-fluoromethyl-4-nitrobenzimidazole is tautomeric and also includes the sodium salt of the 2-fluoroalkyl-5-fluoromethyl-7-nitrobenzimidazole.)

Compounds useful in the insecticidal processes of this invention are prepared as follows.

EXAMPLE I 2,6-Bis(trifluoromethyl)-4-nitrobenzimidazole

A solution of 40.5 g. of 2,6-dinitro-4-trifluoromethyl-1-chlorobenzene in 300 ml. of benzene was mixed with 250 ml. of 14 N ammonium hydroxide. The reaction mixture was stirred at room temperature for about 1.5 hours, at which point in time another 100 ml. of 14 N ammonium hydroxide were added and the stirring was continued for an additional 2 hours. The organic layer was separated, was washed with water and was dried. Removal of the solvents in vacuo yielded 2,6-dinitro-4-trifluoromethylaniline, which melted at about 142°–144° C. after recrystallization from a hexane-benzene solvent mixture.

Twenty-four grams of 2,6-dinitro-4-trifluoromethylaniline were dissolved in 300 ml. of ethanol. The solution was heated to about 35° C. and 110 ml. of a 20 percent ammonium polysulfide solution containing 5 percent free sulfur was added. The temperature of the reaction mixture rose spontaneously to about 60° C., at which temperature it was maintained by heating for about 10 minutes. The reaction mixture was cooled to about 40° C. and poured into water. The resulting mixture was filtered. Excess benzene was added to the filtrate which was then evaporated to dryness in vacuo using the water-benzene azeotrope. Recrystallization of the resulting solid yielded purified 3-nitro-5-trifluoromethyl-o-phenylenediamine melting at about 121°-123° C.

A reaction mixture containing 3 g. of 3-nitro-5-trifluoromethyl-o-phenylenediamine, 10 ml. of trifluoroacetic acid and 25 ml. of water was refluxed for about 4 hours. The reaction product containing 2,6-bis(trifluoromethyl)-4-nitrobenzimidazole was poured into water and stirred until it solidified. The benzimidazole was dissolved in base at pH=11 and the solution filtered. The pH was then lowered to about 7, at which point 2,6-bis(trifluoromethyl)-4-nitrobenzimidazole began to crystallize. The compound was separated by filtration, the filter cake washed with water and then dried. Recrystallization from a benzene-hexane solvent mixture yielded 2,6-bis(trifluoromethyl)-4-nitrobenzimidazole, melting at about 95°-97° C.

Analysis, Calc.: C, 36.13; N, 14.05; H, 1.01; Found: C, 36.24; N, 13.87; H, 1.32

Compounds in which the substituent on the 2-position of the benzimidazole ring is other than trifluoromethyl are prepared by the method of Smith and Stienle, *J. Am. Chem. Soc.* 75, 1292 (1953), which method in this instance involves the heating of an appropriately substituted o-phenylene diamine with trifluoroacetic acid, pentafluoropropionic acid, difluoroacetic acid, heptafluorobutyric acid, or chlorodifluoroacetic acid, optionally in the presence of dilute HCl. 2-Chlorodifluoromethyl-4-nitro-6-trifluoromethylbenzimidazole prepared in this way melts at about 97°-98° C. after recrystallization from hexane.

Analysis, Calc.: C, 34.25; H, 0.96; N, 13.31; Found: C, 34.50; H, 1.01, N, 13.35.

Compounds in which the substituent in the 6(5) position of the benzene ring of the benzimidazole is difluoromethyl are prepared from 2,6-dinitro-4-difluoromethylbenzene according to the above procedure. This latter compound is prepared by the reaction of $SF_4$ and 3,5-dinitro-4-hydroxybenzaldehyde to yield 2,6-dinitro-4-difluoromethylphenol which is converted to the corresponding chloride by conventional means. 2-Trifluoromethyl-4-nitro-6-difluoromethylbenzimidazole was prepared from the above diamine by the process of the above example and melted at about 132°-134° C. after recrystallization from benzene.

Analysis, Calc.: C, 38.44; H, 1.43; N, 14.93; Found: C, 38.30; H, 1.40; N, 14.82.

EXAMPLE II 2,6-Bis(trifluoromethyl)-4-nitro-1-phenylsulfonylbenzimidazole

A solution containing 6.4 g. of anhydrous sodium 2,6-bis(trifluoromethyl)-4-nitrobenzimidazole was prepared in 50 ml. of anhydrous acetonitrile. Three and five tenths grams of benzenesulfonyl chloride and 20 ml. of anhydrous acetonitrile were added. Sodium chloride formed as a by-product in the reaction was separated by filtration and 2,6-bis(trifluoromethyl)-4-nitro-1-phenylsulfonylbenzimidazole thus prepared was isolated by evaporation of the solvent in vacuo. Recrysatallization of the product from a benzenepentane solvent mixture yielded 2,6-bis(trifluoromethyl)-4-nitro-1-phenylsulfonylbenzimidazole melting at about 183°-185° C. Nuclear magnetic resonance spectrum indicated that the desired product had been prepared and that there were no detectabale quantities of impurities present.

EXAMPLE III

Phenyl 2,6-bis(trifluoromethyl)-4-nitro-1-benzimidazolecarboxylate and

Phenyl 2,5-bix(trifluoromethyl)-7-nitro-1-benzimidazolecarboxylate

The procedure of Example II was followed, except that phenyl chloroformate was used in place of benzenesulfonyl chloride. The product was isolated by the procedure of Example II and recrystallized from pentane to yield two fractions, the first melting at 83°-93° C. and the second at 92°-95° C. NMR spectrum indicated that the desired compounds had been prepared substantially free from impurities, although it was not possible to determine which fraction had a particular structure.

Other compounds prepared by the procedure of the above example using the appropriate chloroformate or thiocarbamyl chloride in place of phenyl chloroformate include the following:

benzyl 2,6-bis(trifluoromethyl)-4-nitro-1-benzimidazolecarboxylate, M.P. = 109°-113° C.
p-nitrophenyl 2,6-bis(trifluoromethyl)-4-nitro-1-benzimidazole carboxylate, M.P. = 60°-88° C.
methyl 2,5-bis(trifluoromethyl)-7-nitro-1-benzimidazolecarboxylate, M.P. = 93°-98° C.
methyl 2,6-bis(trifluoromethyl)-4-nitro-1-benzimidazolecarboxylate, M.P. = 93°-98° C.
n-hexyl 2,6-bis(trifluoromethyl)-4-nitro-1-benzimidazolecarboxylate, M.P. = 40°-43° C.
ethyl 2,6-bis(trifluoromethyl)-4-nitro-1-benzimidazolecarboxylate, M.P. = 78°-84° C.
phenyl 2,6-bis(trifluoromethyl)-4-nitro-1-benzimidazolecarboxylate, M.P. = 87°-95° C.
isopropyl 2,6-bis(trifluoromethyl)-4-nitro-1-benzimidazolecarboxylate, M.P. = 49°-55° C.
allyl 2,6-bis(trifluoromethyl)-4-nitro-1-benzimidazolecarboxylate, M.P. 75°-80° C.
N-ethyl-2,6-bis(trifluoromethyl)-4-nitro-benzimidazole-1-thiocarboxanilide, M.P. = 96°-104° C.
4-nitro-1-piperidinothionocarbonyl-2,6-bis(trifluoromethyl)benzimidazole, M.P. = 112°-126° C.
N,N-di-n-propyl-4-nitro2,6-bis(trifluoromethyl)thio-1-benzimidazolecarboxamide, M.P. = 118°-127° C.
N,N-diethyl-4-nitro-2,6-bis(trifluoromethyl)thio-1-benzimidazolecarboxamide, M.P. 140°-143° C.
N,N-dimethyl-4-nitro-2,6-bis(trifluoromethyl)thio-1-benzimidazolecarboxamide, M.P. = 105°-114° C.

Other compounds which can be prepared by the procedure of the above examples include:

2-nitrophenyl 2,6-bis(trifluoromethyl)-4-nitro-1-benzimidazolecarboxylate
2-chlorophenyl 2,6-bis(trifluoromethyl)-4-nitro-1-benzimidazolecarboxylate
3,4-dimethoxyphenyl 2,6-bis(trifluoromethyl)-4-nitro-1-benzimidazolecarboxylate
2,4-xylyl 2,5-bis(trifluoromethyl)-7-nitro-1-benzimidazolecarboxylate
2,6-bis(trifluoromethyl)-4-nitro-1-(4-ethoxyphenylsulfonyl)benzimidazole
2,6-bis(trifluoromethyl)-4-nitro-1-(3-bromophenylsulfonyl)benzimidazole
2,5-bis(trifluoromethyl)-7-nitro-1-(p-tolylsulfonyl)-benzimidazole
4-chlorobenzyl 2,6-bis(trifluoromethyl-4-nitro-1-benzimidazolecarboxylate
2-isopropoxybenzyl 2,6-bis(trifluoromethyl)-4-nitro-1-benzimidazolecarboxylate
4-nitrobenzyl 2,6-bis(trifluoromethyl)-4-nitro-1-benzimidazolecarboxylate
2,4-dinitrobenzyl 2,5-bis(trifluoromethyl)-7-nitro-1-benzimidazolecarboxylate
3-chloro-4-methylbenzyl 2,6-bis(difluoromethyl)-4-nitro-1-benzimidazolecarboxylate
sec-butyl 2,6-bis(trifluoromethyl)-4-nitro-1-benzimidazolecarboxylate
isooctyl 2,5-bis(trifluoromethyl)-7-nitro-1-benzimidazolecarboxylate
2-chloroheptyl 2,6-bis(trifluoromethyl)-4-nitro-1-benzimidazolecarboxylate
perfluoropentyl 2,6-bis(trifluoromethyl)-4-nitro-1-benzimidazolecarboxylate
2-bromoallyl 2,5-bis(difluoromethyl)-7-nitro-1-benzimidazolecarboxylate
2-butynyl 2,6-bis(trifluoromethyl)-4-nitro-1-benzimidazolecarboxylate
2-pentenyl 2,5-bis(trifluoromethyl)-7-nitro-1-benzimidazolecarboxylate
neopentyl 2,6-bis(trifluoromethyl)-4-nitro-1-benzimidazolecarboxylate
3,4-dimethoxyphenethyl 2,5-bis(difluoromethyl)-7-nitro-1-benzimidazolecarboxylate
2-(o-fluorophenyl)-2-methylethyl 2,5-bis(trifluoromethyl)-7-nitro-1-benzimidazolecarboxylate
p-(t-butyl)benzyl 2,6-bis(trifluoromethyl)-4-nitro-1-benzimidazolecarboxylate
4-fluorophenyl 2,6-bis(trifluoromethyl)-4-nitro-1-benzimidazolecarboxylate
3,4-dichlorophenyl 2,6-bis(difluoromethyl)-4-nitro-1-benzimidazolecarboxylate
2-chloro-4-nitrophenyl 2,5-bis(trifluoromethyl)-7-nitro-1-benzimidazolecarboxylate
butadienyl 2,5-bis(trifluoromethyl)-7-nitro-1-benzimidazolecarboxylate
p-isopropylphenyl 2,6-bis(trifluoromethyl)-4-nitro-1-benzimidazolecarboxylate
o-(n-pentyl)phenyl 2,5-bis(trifluoromethyl)-7-nitro-1-benzimidazolecarboxylate
p-(t-butyl)phenyl 2,5-bis(trifluoromethyl)-7-nitro-1-benzimidazolecarboxylate
p-(n-butoxy)phenyl 2,6-bis(trifluoromethyl)-4-nitro-1-benzimidazolecarboxylate
2-pentafluoroethyl-4-nitro-6-difluoromethylbenzimidazole
2-heptafluoropropyl-4-nitro-6-difluoromethylbenzimidazole
2-chlorodifluoromethyl-4-nitro-6-difluoromethylbenzimidazole
2,6-bis(difluoromethyl)-4-nitro-benzimidazole
4-nitro-1-pyrrolidinothionocarbonyl-2-pentafluoroethyl-6-trifluoromethylbenzimidazole
3-pentenyl 4-nitro-2-chlorodifluoromethyl-6-trifluoromethyl-1-benzimidazolecarboxylate
phenyl 2-pentafluoroethyl-4-nitro-6-difluoromethyl-1-benzimidazolecarboxylate
o-tolyl-2-difluoromethyl-7-nitro-5-trifluoromethyl-1-benzimidazolecarboxylate
4-bromobenzyl 2-heptafluoropropyl-7-nitro-5-trifluoromethyl-1-benzimidazolecarboxylate
1-o-tolylsulfonyl-2-difluoromethyl-4-nitro-6-trifluoromethylbenzimidazole
homoveratryl 2-chlorodifluoromethyl-4-nitro-6-difluoromethyl-1-benzimidazolecarboxylate
ethyl 2-chlorodifluoromethyl-4-nitro-6-trifluoromethyl-1-benzimidazolecarboxylate Most of the compounds within the scope of Formula I above are phytotoxic at application rates considerably higher than those at which the compounds are insecticidally active and many are effective herbicides for a wide variety of plants at application rates 8 lbs. per acre or higher. However, the extreme effectiveness of the insecticides represented by Formula I provides a sufficient margin of safety to enable their use, either in the soil in the presence of growing or seedling crops, or by a one-time application to the foliage, as agricultural insecticides.

EXAMPLE IV

Preparation of Salts

A mixture is prepared containing 6 g. of 2,6-bis(trifluoromethyl)-4-nitrobenzimidazole, 1.1 g. of sodium methoxide and 100 ml. of methanol. The reaction mixture is shaken and filtered. Evaporation of the filtrate to dryness yields a mixture of the sodium salt of 2,6-bis(trifluoromethyl)-4-nitrobenzimidazole and the sodium salt of 2,5-bis(trifluoromethyl)-7-nitrobenzimidazole, melting at about 200° C. The compound is water soluble, but insoluble in acid.

Other alkali metal or alkaline earth salts of 2,6-bis(trifluoromethyl)-4-nitrobenzimidazole are prepared by substituting the appropriate metal alkoxide for sodium methoxide in the above preparation. Thus, the lithium, potassium, caesium, rubidium, strontium, barium, calcium and magnesium salts of 2,6-bis(trifluoromethyl)-4-nitrobenzimidazole (and its tautomer) can be prepared.

While the compounds of this invention resemble the organic phosphates in being toxic upon ingestion, they differ from the organic phosphates in having a low toxicity when applied to the skin. The following charts give the estimated acute oral and acute dermal toxicities of 2,6-bis(trifluoromethyl)-4-nitrobenzimidazole in several species of mammals.

TABLE 10

Acute Oral Toxicity of 2,6-bis(trifluoromethyl)-4-nitrobenzimidazole

| Animals Used | Est. $LD_{50}$, mg./kg. |
|---|---|
| Mouse, female | 27 |
| Rat, male | 16–20 |
| Rat, female | 19–22 |
| Guinea Pig, male | 15 |
| Guinea Pig, female | 15 |

TABLE 11
Acute Dermal Toxicity of 2,6-bis(tri-fluoromethyl)-4-nitrobenzimidazo

| Animals Used | Est. $LD_{50}$, mg./kg. |
|---|---|
| Rabbit, male | >500 |
| Rabbit, female | >500 |

A group of highly active insecticides and miticides coming within the scope of Formula I consists of 2,6(5)-bis(trifluoromethyl)-4(7)-nitrobenzimidazole and its $N^1$ derivatives as represented by Formula IV below.

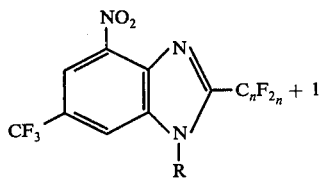

IV wherein R, R', R", R''' and R'''' have the same meaning as hereinabove, and n is 1-3. The use of the compounds of Formula IV as insecticides and miticides constitutes a preferred process of this invention.

I claim:

1. A method for killing insects of the order Coleoptera comprising the application to an insect habitat insecticidally effective amount of a benzimidazole represented by the following formula:

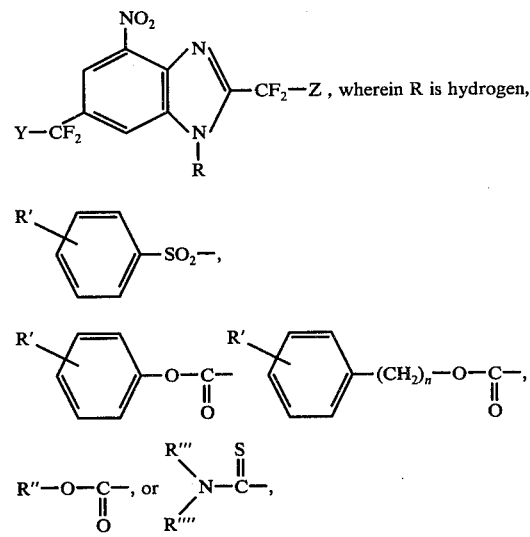

wherein R' is hydrogen, fluorine, chlorine, bromine, $C_1$-$C_5$ alkoxy, $C_1$-$C_5$ alkyl or nitro; and R" is $C_1$-$C_8$ alkyl, halo-substituted $C_1$-$C_5$ alkyl, halo-substituted $C_2$-$C_5$ alkynyl or $C_2$-$C_5$ alkenyl; R''' and R'''' individually are hydrogen, $C_1$-$C_5$ alkyl or phenyl, and when taken together a pentamethylene or tetramethylene chain; and Y is F or H; Z is F, H, Cl, —$CF_3$ or —$CF_2$—$CF_3$; n is 1-3; and halo is a halogen having an atomic number below 36.

2. A method according to claim 1 wherein the compound applied is 2,6-bis(trifluoromethyl)-4-nitrobenzimidazole.

3. A method according to claim 1 wherein the compound applied is isopropyl 2,6-bis(trifluoromethyl)-4-nitro-1-benzimidazolecarboxylate.

4. A method according to claim 1 wherein the compound applied is 2,6-bis(trifluoromethyl)-4-nitro-1-phenylsulfonylbenzimidazole.

5. A method according to claim 1 wherein the compound applied is allyl 2,6-bis(trifluoromethyl)-4-nitro-1-benzimidazolecarboxylate.

6. A method according to claim 1 wherein the compound applied is 2-chlorodifluoromethyl-4-nitro-6-trifluoromethylbenzimidazole.

7. A method according to claim 1 wherein the compound applied is 2-trifluoromethyl-4-nitro-6-difluoromethylbenzimidazole.

8. A method for killing insects of the order Coleoptera comprising the application to an insect habitat of a insecticidally effective amount of a benzimidazole represented by the following formula:

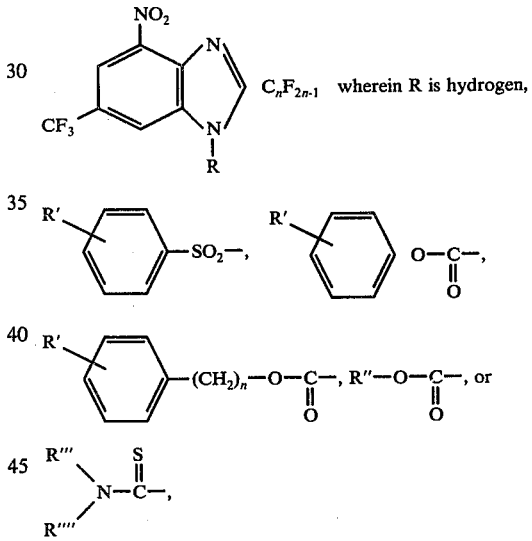

wherein R' is hydrogen, halogen having an atomic number below 36, $C_1$-$C_5$ alkoxy, $C_1$-$C_5$ alkyl or nitro; and R" is $C_1$-$C_8$ alkyl, halo-substituted $C_1$-$C_8$ alkyl, halo-substituted $C_2$-$C_5$ alkenyl, $C_2$-$C_5$ alkynyl or $C_2$-$C_5$ alkenyl; n is 1-3; halo is a halogen having an atomic number below 36; and R''' and R'''' are individually hydrogen, $C_1$-$C_5$ alkyl or phenyl and when taken together a pentamethylene or tetramethylene chain.

* * * * *